(12) United States Patent
Graff et al.

(10) Patent No.: US 6,646,003 B2
(45) Date of Patent: Nov. 11, 2003

(54) METHOD OF TREATING OCULAR INFLAMMATORY AND ANGIOGENESIS-RELATED DISORDERS OF THE POSTERIOR SEGMENT OF THE EYE USING AN AMIDE DERIVATIVE OF FLURBIPROFEN OR KETOROLAC

(75) Inventors: Gustav Graff, Cleburne, TX (US); Mark R. Hellberg, Highland Village, TX (US); John M. Yanni, Burleson, TX (US)

(73) Assignee: Alcon, Inc., Hunenberg (CH)

(*) Notice: Subject to any disclaimer, the term of this patent is extended or adjusted under 35 U.S.C. 154(b) by 72 days.

(21) Appl. No.: 10/092,969

(22) Filed: Mar. 7, 2002

(65) Prior Publication Data

US 2002/0183376 A1 Dec. 5, 2002

Related U.S. Application Data

(60) Provisional application No. 60/280,886, filed on Apr. 2, 2001.

(51) Int. Cl.$^7$ .................... A61K 31/24; A61K 31/19
(52) U.S. Cl. ............... 514/535; 514/570; 514/617; 514/618; 514/619; 514/621; 514/912
(58) Field of Search ............... 514/535, 570, 514/617, 618, 619, 621, 912

(56) References Cited

U.S. PATENT DOCUMENTS

| | | | |
|---|---|---|---|
| 3,755,427 A | 8/1973 | Adams et al. | 260/515 A |
| 3,793,457 A | 2/1974 | Adams et al. | 424/317 |
| 3,828,093 A | 8/1974 | Bays et al. | 260/469 |
| 4,045,576 A | 8/1977 | Welstead, Jr. et al. | 424/309 |
| 4,126,635 A | 11/1978 | Welstead, Jr. et al. | 562/441 |
| 4,182,774 A | 1/1980 | Welstead, Jr. et al. | 424/309 |
| 4,230,724 A | 10/1980 | Cooper et al. | 424/317 |
| 4,254,146 A | 3/1981 | Walsh | 424/309 |
| 4,313,949 A | 2/1982 | Shanklin, Jr. et al. | 424/248.56 |
| 4,371,473 A | 2/1983 | Zaiko et al. | 260/465 |
| 4,422,979 A | 12/1983 | Zaiko et al. | 260/465 |
| 4,454,151 A | 6/1984 | Waterbury | 424/274 |
| 4,503,073 A | 3/1985 | Walsh et al. | 514/539 |
| 4,568,695 A | 2/1986 | Moran et al. | 514/648 |
| 4,613,505 A | 9/1986 | Mizushima et al. | 424/80 |
| 4,683,242 A | 7/1987 | Poser | 514/539 |
| 4,783,487 A | 11/1988 | Brune | 514/563 |
| 4,851,443 A | 7/1989 | Brune | 514/563 |
| 4,910,225 A | 3/1990 | Ogawa et al. | 514/561 |
| 4,988,728 A | 1/1991 | Gerson et al. | 514/448 |
| 4,996,209 A | 2/1991 | Aoki | 514/263 |
| 5,073,641 A | 12/1991 | Bundgaard et al. | 560/56 |
| 5,171,566 A | 12/1992 | Mizushima et al. | 424/78.04 |
| 5,475,034 A | 12/1995 | Yanni et al. | 514/619 |
| 5,681,964 A | 10/1997 | Ashton et al. | 548/491 |
| 5,807,568 A | 9/1998 | Cody et al. | 424/444 |
| 5,814,655 A | 9/1998 | Patel et al. | 514/413 |
| 6,416,777 B1 * | 7/2002 | Yaacobi | 424/428 |

FOREIGN PATENT DOCUMENTS

| | | |
|---|---|---|
| EP | 0 592 348 A1 | 10/1993 |
| GB | 2 071 086 A | 9/1981 |
| GB | 2 093 027 A | 8/1982 |
| WO | WO 00/40087 | 7/2000 |

OTHER PUBLICATIONS

Graff et al., "Characterization of In Vitro Corneal Penetration, Bioactivation and Topical Ocular Anti–inflammatory Activity of Nepafenac and Amide Analogs of Classical NSAIDs," Association for Research in Vision and Ophthalmology Meeting; Ft. Lauderdale, Florida; Mar., 2001.
Sancilio et al., "AHR–10037, a non–steroidal anti–inflammatory compound of low gastric toxicity," Agents and Actions, 31:117–126 (1990).
Walsh et al., "Antiinflammatory Agents. 3. Synthesis and Pharmacological Evaluation of 2–Amino–3–benzoyl phenylacetic Acid and Analogues," J. Med. Chem. 27:1379–1388 (1984).
Walsh et al., "Antiinflammatory Agents. 4. Syntheses and Biological Evaluation of Potential Prodrugs of 2–Amino–3–benzoylbenzeneacetic Acid and 2–Amino–3–(4–chlorobenzoyl)benzeneacetic Acid," J. Med. Chem. 33:2296–2304 (1990).
Merck Index 12$^{th}$ Edition, Merck Research Laboratories, Whitehouse Station, NJ, (1996) p. 712 ("flurbiprofen").
Merck Index 12th Edition, Merck Research Laboratories, Whitehouse Station, NJ, (1996) p. 905 ("ketorolac").
Nonsteroidal Anti–inflammatory Agents, Ophthalmic Drug Facts, pp. 79–82 (1993).
Gamache et al., "Nepafenac, a Unique Nonsteroidal Prodrug with Potential Utility in the Treatment of Trauma–Induced Ocular Inflammation: I. Assessment of anti–Inflammatory efficacy," Inflammation, vol. 24(4), pp. 357–369 (2000).
Ke et al., "Nepafenac, a Unique Nonsteroidal Prodrug with Potential Utility in the Treatment of Trauma–Induced Ocular Inflammation: II. In Vitro Bioactivation and Permeation of External Ocular Barriers," Inflammation, vol. 24(4), pp. 371–384 (2000).
Solomon et al., "Efficacy of Topical Flurbiprofen and Indomethacin in Preventing Pseudophakic Cystoid Macular Edema," J. Cataract Refractive Surgery, vol. 21, pp. 73–81 (1995).

* cited by examiner

Primary Examiner—Zohreh Fay
(74) Attorney, Agent, or Firm—Patrick M. Ryan

(57) ABSTRACT

The topical use of certain flurbiprofen amide derivatives and ketorolac amide derivatives to treat ophthalmic angiogenesis-related and inflammatory disorders of the posterior segment of the eye is disclosed.

8 Claims, No Drawings

METHOD OF TREATING OCULAR INFLAMMATORY AND ANGIOGENESIS-RELATED DISORDERS OF THE POSTERIOR SEGMENT OF THE EYE USING AN AMIDE DERIVATIVE OF FLURBIPROFEN OR KETOROLAC

This application claims priority from U.S. Provisional application, U.S. Ser. No. 60/280,886, filed Apr. 2, 2001.

FIELD OF THE INVENTION

This invention relates to the treatment of ophthalmic disorders. In particular, this invention relates to the topical use of certain amide derivatives of flurbiprofen or ketorolac to treat or prevent ophthalmic inflammatory and angiogenesis-related disorders of the posterior segment of the eye.

BACKGROUND OF THE INVENTION

U.S. Pat. No. 3,755,427 discloses that the compound known as "flurbiprofen" and certain related compounds possess anti-inflammatory, analgesic and antipyretic properties and are useful for the treatment of anti-inflammatory conditions, conditions of pain, and pyretic conditions. The '427 patent discloses therapeutic compositions comprising a compound of the invention in association with pharmaceutical excipients known for the production of compositions for oral, topical, rectal or parenteral administration. The compositions are preferably administered orally (see Col. 4, lines 58–62). According to the '427 patent at Col. 4, lines 63–69, "salts, esters, amides and alcohols derived from a compound of the invention may be used in place of a compound of the invention as such derivatives appear to be metabolised by the animal body" and converted into the corresponding acid.

The topical use of flurbiprofen and ketorolac to treat ophthalmic inflammatory conditions is known. Flurbiprofen sodium is sold as topically administrable eye drops, including a product sold under the trade name OCUFEN® (Allergan, Inc., Irvine, Calif.). In addition, U.S. Pat. No. 4,996,209 discloses the use of S(+)-flurbiprofen, substantially free of its enantiomer, R(–)-flurbiprofen, as a topical ophthalmic antiinflammatory agent. Currently, however, no topically administrable amide derivative of flurbiprofen is sold for the treatment of ophthalmic disorders. Ketorolac tromethamine is sold as topically administrable eye drops under the trade name ACULAR® (Allergan, Inc., Irvine, Calif.).

U.S. Pat. No. 4,454,151 discloses the use of ketorolac and certain related acids, salts and esters for relieving, inhibiting or preventing ophthalmic diseases in mammals. Definitions of salts and esters are provided in the '151 patent at column 3, lines 25–42. The ophthalmic diseases may be, among others, glaucoma, cystoid macular edema, uveitis, diabetic retinopathy, conjunctivitis, or any trauma caused by eye surgery or eye injury and which are either caused by, associated with, or accompanied by inflammatory processes. Among other ways, the compounds of the '151 patent may be administered topically to the eye in the form of eye drops.

U.S. Pat. No. 4,230,724 discloses a method of treating vascularization of the eye as a result of traumatic injury, surgery (such as a corneal transplant procedure) or onset of diabetic retinopathy, by topically treating the eye with flurbiprofen or a pharmaceutically acceptable salt thereof.

Amide derivatives of certain ophthalmically administrable non-steroidal anti-inflammatory drugs ("NSAIDS") are known. For example, U.S. Pat. No. 5,475,034 discloses topically administrable compositions containing certain amide and ester derivatives of 3-benzyolphenylacetic acid, including nepafenac, useful for treating ophthalmic inflammatory disorders and ocular pain. According to the '035 patent at Col. 15, lines 35–39, "[s]uch disorders include, but are not limited to uveitis scleritis, episcleritis, keratitis, surgically-induced inflammation and endophthalmitis."

SUMMARY OF THE INVENTION

It has now been found that certain amide derivatives of flurbiprofen and ketorolac are unexpectedly effective in treating or preventing ophthalmic inflammatory and angiogenesis-related disorders of the posterior segment of the eye when topically administered to the eye.

Among other factors, the present invention is based on the finding that amide derivatives of some ophthalmically acceptable NSAIDS are not hydrolytically bioactivated while others are. Without being bound to any theory, it is believed that ocular tissue hydrolases, particularly the hydrolases of the iris/ciliary body are selective in their ability to bioactivate or hydrolyze amide derivatives of arylacetic acid NSAIDS.

DETAILED DESCRIPTION OF THE INVENTION

The amide derivatives of flurbiprofen and ketorolac useful in the methods of the invention are those of formulas (I) and (II) below.

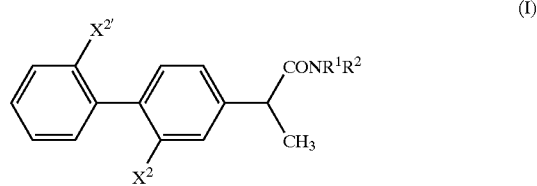

(I)

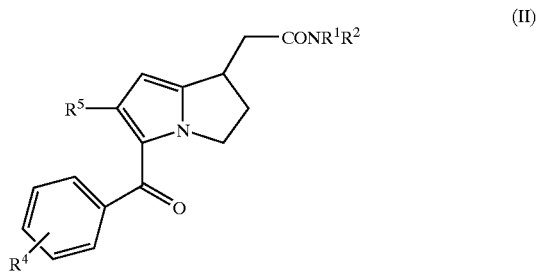

(II)

wherein $R^1$=H, $C_{1-6}$(un)branched alkyl, (un)substituted (substitution as defined by Z below), —$(CH_2)_n$—X—$(CH_2)_{n'}$A;

$R^2$=H, $C_{1-3}$ alkyl, $OR^3$;

$R^3$=H, $C_{1-3}$ alkyl;

$R^4$=H, Me—, MeO—, MeS—;

$R^5$=H, Me—;

X=nothing (carbon—carbon bond), O, C=O, OC(=O), C(=O)O, C(=O)$NR^3$, $NR^3$C(=O), $S(O)_{n2}$, $CHOR^3$, $NR^3$;

$X^2$, $X^{2'}$ independently=H, F;

n=2–6;

n'=1–6;

$n^2$=0–2;

A=H, OH, optionally (un)substituted aryl (substitution as defined by Z below), (un)substituted heterocycle (substitution as defined by Z below); and Z=H, Cl, F, Br, I, $OR^3$, CN, OH, $CF_3$, $R^4$, $NO_2$.

The compounds of formulas (I) and (II) can readily be made by one skilled in the art. For example, amide derivatives of formulas (I) and (II) can be prepared by reacting flurbiprofen or ketorolac with the appropriate amine derivative in the presence of a coupling agent such as dicyclohexylcarbodiimide or 1-(3-dimethylamino-propyl)-3-ethyl carbodiimide HCl, and 4-dimethylaminopyridine or 1-hydroxybenzotriazole, in an organic solvent such as acetonitrile, tetrahydrofuran or dimethylformamide at temperatures from 0° C. to 50° C. The use of certain protecting groups and deprotecting steps may be necessary, as appreciated by those skilled in the art.

Preferred compounds of formulas (I) and (II) for use in the methods of the present invention are those wherein:

$R^1$=H, $C_{1-4}$(un)branched alkyl, (un)substituted (substitution as defined by Z below);

$R^2$, $X^{2'}$, $R^4$, $R^5$=H;

$X^2$=F; and

Z=Cl, F, Br, OH.

More preferred are compounds of formulas (I) and (II) wherein $R^1$=H, $C_{1-3}$ alkyl. The most preferred compound of formula (I) for use in the methods of the present invention is 2-(3-fluoro-4-phenyl)-propionamide. The most preferred compound of formula (II) for use in the methods of the present invention is 5-benzoyl-2,3-dihydro-1H-pyrrolizine-1-carboxamide.

According to the present invention, a therapeutically effective amount of a compound of formula (I) or (II) is administered topically to the eye to treat or prevent ophthalmic inflammatory and angiogenesis-related disorders of the posterior segment of the eye. Such disorders include, but are not limited to, surgically-induced inflammation of the posterior segment of the eye; trauma-induced inflammation of the posterior segment of the eye; cystoid macular edema; exudative macular degeneration; proliferative diabetic retinopathy; ischemic retinopathies (e.g., retinal vein or artery occlusion); retinopathy of prematurity; iritis rubeosis; cyclitis; and sickle cell retinopathy.

The compounds of formula (I) and (II) can be formulated into a variety of topically administrable ophthalmic compositions, such as solutions, suspensions, gels or ointments. The most preferred form of delivery is by aqueous eye drops, but gels or ointments can also be used. Aqueous eye drops, gels and ointments can be formulated according to conventional technology and would include one or more excipients. For example, topically administrable compositions may contain tonicity-adjusting agents, such as mannitol or sodium chloride; preservatives such as chlorobutanol, benzalkonium chloride, polyquaternium-1, or chlorhexidine; buffering agents, such as phosphates, borates, carbonates and citrates; and thickening agents, such as high molecular weight carboxy vinyl polymers, including those known as carbomers, hydroxyethylcellulose, or polyvinyl alcohol.

The amount of the compound of formula (I) or (II) used in the treatment or prevention of ophthalmic disorders according to the present invention will depend on the type of disorder to be prevented or treated, the age and body weight of the patient, and the form of preparation. Compositions intended for topical ophthalmic administration as eye drops will typically contain a compound of formula (I) in an amount of from about 0.001 to about 4.0% (w/w), preferably from about 0.01 to about 0.5% (w/w), with 1–2 drops instilled once to several times a day.

Additional therapeutic agents may be added to supplement or complement the compounds of formula (I) and (II).

The following examples are presented to illustrate various aspects of the present invention, but are not intended to limit the scope of the invention in any respect. The percentages are expressed on a weight/volume basis.

EXAMPLE 1

The following formulations are representative of the topical compositions useful in the present invention.

| Formulation 1 | |
| --- | --- |
| Compound of formula (I) or (II) | 0.01–0.5% |
| Polysorbate 80 | 0.01% |
| Benzalkonium Chloride | 0.01% + 10% excess |
| Disodium EDTA | 0.1% |
| Monobasic Sodium Phosphate | 0.03% |
| Dibasic Sodium Phosphate | 0.1% |
| Sodium Chloride | q.s. 290–300 mOsm/Kg |
| pH adjustment with NaOH and/or HCl | pH 6.0–7.6 |
| Water | q.s. 100% |
| Formulation 2 | |
| Compound of formula (I) or (II) | 0.01–0.5% |
| Hydroxypropyl Methylcellulose | 0.5% |
| Polysorbate 80 | 0.01% |
| Benzalkonium Chloride | 0.01% + 5% excess |
| Disodium EDTA | 0.01% |
| Dibasic Sodium Phosphate | 0.2% |
| Sodium Chloride | q.s. 290–300 mOsm/Kg |
| pH adjustment with NaOH and/or HCl | pH 6.0–7.6 |
| Water | q.s. 100% |

EXAMPLE 2

The in vitro corneal permeability, bioactivation (hydrolysis) and in vivo antiinflammatory activity of amide derivatives of flurbiprofen (2-(3-fluoro-4-phenyl)-propionamide); bromfenac (N-methyl 2-amino-3-(4-bromobenzoyl)benzeneacetamide; N,N-dimethyl 2-amino-3-(4-bromobenzoyl)benzeneacetamide; diclofenac (2-[2,6-dichlorophenyl)amino]benzeneacetamide); suprofen (α-methyl-4-(2-thienylcarbonyl)-benzeneacetamide); ketorolac (5-benzoyl-2,3-dihydro-1H-pyrrolizine-1-carboxamide); and amfenac (2-amino-3-benzoyl) benzeneacetamide; nepafenac) were compared.

Methods: in vitro Corneal Drug Permeation

Freshly excised corneas were obtained from 6-week old NZA rabbits (1.3–1.5 kg). Corneas were mounted in a modified Lucite perfusion chamber and perfused with glutathione-supplemented bicarbonated Ringer (GBR) buffer as previously described[1]. Drug concentrations in GBR buffer were as indicated (FIG. 1), with the corneal epithelial cell layer facing the drug containing donor compartment. The final volume of the donor and receiver side of the perfusion chamber was 7.0 mL. Samples of 0.1 mL were withdrawn from both chambers at the beginning of the experiment and at 20 to 30 minute intervals thereafter through six hours. Samples were mixed with an equal volume of methanol and immediately subjected to HPLC analysis. HPLC analysis was carried out on a 25 cm×4.6 mm I.D. Spherosorb RP-18, 10µ column at a flow rate of 2.0 ml/min. The column effluent was monitored with a flow monitor at a wavelength of 230 nm. Elution of NSAID free acids and amides was accomplished with an eluant mixture composed of methanol:water:phosphoric acid (60/40/1 (v/v/ v)) (pH 3.0). The eluant mixture was changed to methanol:water:phosphoric acid (60/40/1 (v/v/v)) (pH 3.0) when suprofen and suprofen amide were subjected to HPLC analysis.

In vitro Metabolism

Freshly dissected iris/ciliary body from the NZA rabbit was incubated at 36° C. for a period of four to six hours in 0.5 ml of GBR buffer (pH 7.6) supplemented with amide derivatives of the indicated NSAIDs. The drug concentrations used were as indicated in FIG. 2. Samples of 0.1 ml were removed for HPLC analysis to monitor the hydrolytic conversion of NSAID amides to free carboxylic acids.

Inhibition of Trauma-Induced Ocular Inflammation

Effects of a single prophylactic topical ocular dose of the tested compounds were examined in a rabbit model of paracentesis (Graff, et al., *Ocular Immunol. Inflamm.*, 6:227–238 (1998)). Briefly, a single 50 μL drop of a 0.1% drug solution/suspension was administered topically onto the eye 45 minutes prior to paracentesis and removal of ~150 μL of aqueous humor. Thirty minutes after execution of paracentesis aqueous humor was removed (~100 μL) for analysis. Both pre- and post-paracentesis samples were assayed for protein and $PGE_2$ content.

Results

Under conditions of continued drug perfusion of the corneal epithelium, the amide derivatives of amfenac and diclofenac exhibited similar permeation coefficients (7.4 $cm/min^{-1} \times 10^{-5}$ and 7.8 $cm/min^{-1} \times 10^{-5}$, respectively). Lower permeation coefficients (3.7–5.7 $cm/min^{-1} \times 10^{-5}$) were determined for the amide derivatives of flurbiprofen, suprofen, bromfenac and its corresponding monomethyl and dimethyl amide analogs. Assessment of drug hydrolysis by the ICB demonstrated the highest rate for the amide derivative of ketorolac (2.42 nM/min/mg tissue), followed by the amide derivatives of amfenac (0.69 nM/min/mg tissue), flurbiprofen (0.29 nM/min/mg tissue), bromfenac (0.17 nM/min/mg tissue), and its monomethyl amide derivative (0.16 nM/min/mg tissue). Notably, the amide derivatives of suprofen and diclofenac and the dimethyl amide derivative of bromfenac were resistant to hydrolytic bioactivation. Rates of drug hydrolysis by the ICB correlated well with topical ocular in vivo antiinflammatory activity, as indicated by suppression of paracentesis-induced breakdown of the BAB at 0.1%. While no antiinflammatory effects were detectable for the amide derivative of diclofenac and the dimethyl amide derivative of bromfenac, significant inhibition of the BAB was evident for the amide derivatives of flurbiprofen (29% inhibition; vs. 50% inhibition for its free acid analog, flurbiprofen) and amfenac (64%).

This invention has been described by reference to certain preferred embodiments; however, it should be understood that it may be embodied in other specific forms or variations thereof without departing from its special or essential characteristics. The embodiments described above are therefore considered to be illustrative in all respects and not restrictive, the scope of the invention being indicated by the appended claims rather than by the foregoing description.

We claim:

1. A method of treating an ophthalmic inflammatory or angiogenesis-related disorder of the posterior segment of the eye in a patient suffering from or predisposed to such a disorder which comprises topically administering to the eye of the patient a therapeutically effective amount of a compound having the formula (I) or (II):

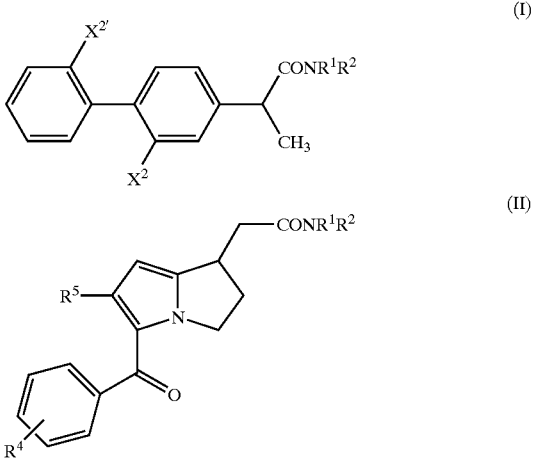

wherein
$R^1$=H, $C_{1-6}$(un)branched alkyl, (un)substituted (substitution as defined by Z below), —$(CH_2)_n$—X—$(CH_2)_{n'}$A;
$R^2$=H, $C_{1-3}$ alkyl, $OR^3$;
$R^3$=H, $C_{1-3}$ alkyl;
$R^4$=H, Me—, MeO—, MeS—;
$R^5$=H, Me—;
X=nothing (carbon—carbon bond), O, C=O, OC(=O), C(=O)O, C(=O)$NR^3$, $NR^3$C(=O), $S(O)_{n2}$, $CHOR^3$, $NR^3$;
$X^2$, $X^{2'}$ independently=H, F;
n=2–6;
n'=1–6;
$n^2$=0–2;
A=H, OH, optionally (un)substituted aryl (substitution as defined by Z below), (un)substituted heterocycle (substitution as defined by Z below); and
Z=H, Cl, F, Br, I, $OR^3$, CN, OH, $CF_3$, $R^4$, $NO_2$.

2. The method of claim 1 wherein
$R^1$=H, $C_{1-4}$(un)branched alkyl, (un)substituted (substitution as defined by Z below);
$R^2$, $X^{2'}$, $R^4$, $R^5$=H;
$X^2$=F; and
Z=Cl, F, Br, OH.

3. The method of claim 2 wherein $R^1$=H, $C_{1-3}$ alkyl.

4. The method of claim 3 wherein the compound is 2-(3-fluoro-4-phenyl)-propionamide.

5. The method of claim 3 wherein the compound is 5-benzoyl-2,3-dihydro-1H-pyrrolizine-1-carboxamide.

6. The method of claim 1 wherein the therapeutically effective amount of the compound is from about 0.001 to about 4.0% (w/v).

7. The method of claim 1 wherein the disorder is selected from the group consisting of exudative macular degeneration; proliferative diabetic retinopathy; ischemic retinopathies; retinopathy of prematurity; iritis rubeosis; cyclitis; and sickle cell retinopathy.

8. The method of claim 1 wherein the disorder is selected from the group consisting of surgically-induced inflammation of the posterior segment of the eye; trauma-induced inflammation of the posterior segment of the eye; and cystoid macular edema.

* * * * *

UNITED STATES PATENT AND TRADEMARK OFFICE
CERTIFICATE OF CORRECTION

PATENT NO. : 6,646,003 B2  
APPLICATION NO. : 10/092969  
DATED : November 11, 2003  
INVENTOR(S) : Graff et al.

Page 1 of 1

It is certified that error appears in the above-identified patent and that said Letters Patent is hereby corrected as shown below:

Column 2, line 41, and Col. 6, line 11, the chemical structure

" 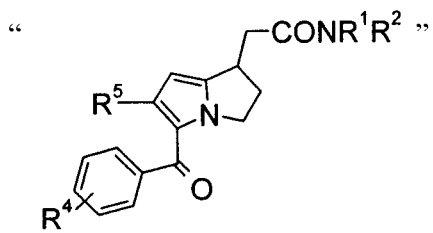 "

should read

-- 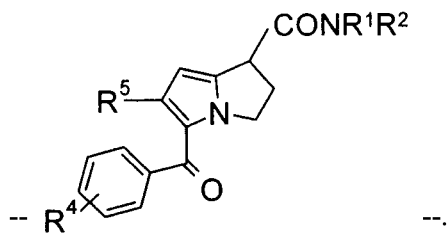 --.

Signed and Sealed this

Tenth Day of October, 2006

JON W. DUDAS  
*Director of the United States Patent and Trademark Office*